(12) United States Patent
Ong et al.

(10) Patent No.: US 7,364,043 B2
(45) Date of Patent: Apr. 29, 2008

(54) FASTENER INSPECTION SYSTEM

(75) Inventors: Hock Seh Ong, Singapore (SG); Ta Seng Jeffrey Mah, Singapore (SG)

(73) Assignee: Zen Voce Manufacturing Pte Ltd, Singapore (SG)

( * ) Notice: Subject to any disclaimer, the term of this patent is extended or adjusted under 35 U.S.C. 154(b) by 808 days.

(21) Appl. No.: 10/747,441

(22) Filed: Dec. 30, 2003

(65) Prior Publication Data

US 2005/0155915 A1  Jul. 21, 2005

(51) Int. Cl.
*B07C 9/00* (2006.01)

(52) U.S. Cl. .................. 209/652; 209/939; 209/938; 209/919; 209/920; 209/650; 209/577; 209/576

(58) Field of Classification Search ................ 209/938, 209/939, 561, 576, 577, 919, 920, 652, 650; 198/395, 397.05, 401
See application file for complete search history.

(56) References Cited

U.S. PATENT DOCUMENTS

| | | | |
|---|---|---|---|
| 4,457,622 A | | 7/1984 | Kato et al. |
| 4,598,998 A | | 7/1986 | Kamei et al. |
| 4,823,396 A | | 4/1989 | Thompson |
| 4,969,746 A | * | 11/1990 | McConnell et al. ........ 356/601 |
| 5,746,323 A | * | 5/1998 | Dragotta ..................... 209/539 |
| 5,823,356 A | | 10/1998 | Goodrich et al. |
| 6,294,747 B1 | * | 9/2001 | Liu et al. ..................... 209/574 |
| 6,787,724 B2 | * | 9/2004 | Bennett et al. ............. 209/586 |

\* cited by examiner

*Primary Examiner*—Kathy Matecki
*Assistant Examiner*—Terrell Matthews
(74) *Attorney, Agent, or Firm*—Lawrence Y D Ho & Associates Pte. Ltd

(57) ABSTRACT

A high-speed fastener inspection system is provided to perform 100 percent inspection of various geometry features and to sort a large number of fasteners at high speed. The inspection system includes a rotary table having an outer periphery, an inner periphery, and a plurality of radial slots extending from the outer periphery to the inner periphery. When a fastener is be placed in a radial slot with the head of the fastener facing upward and the shank extending into the slot, the side view of each fastener is unobstructed. A loading mechanism, an anti-jam mechanism, and a sorting mechanism are arranged along the outer periphery of the rotary table. At least one vision inspection camera is provided for capturing the image of each fastener after each fastener is placed in a radial slot. An image analyzer is operatively connected to the vision inspection camera for analyzing the captured image and to determine whether the fastener is defective. Once the defective fastener has been identified by the image analyzer, the sorting mechanism is actuated to remove the defective fastener from the rotary table.

13 Claims, 6 Drawing Sheets

FASTENER INSPECTION SYSTEM

BACKGROUND OF THE INVENTION

1. Field of the Invention

The invention relates generally to a system and a method for inspecting fasteners, such as screws.

2. Description of the Prior Art

In assembly operations where fasteners such as threaded screws are automatically installed by a machine, defective fasteners cause damage to the product being assembled, resulting in costly repairs. Thus, it is critical for quality control to inspect fasteners for surface flaws prior to use. In the past, fasteners have been manually and visually inspected by workers. However, threaded fasteners are normally made at a high volume, e.g. several thousand fasteners per hour. Visual inspection to sort out defected fasteners from such high volume production has been known to be very time consuming and lacking in adequate precision. Sampling programs were implemented for monitoring the quality of high volume production of threaded fasteners. However, recent zero defect demands for threaded fasteners by the end users have resulted in the requirement that the fastener suppliers inspect 100 percent of the threaded fasteners prior to shipping to the end users. Statistical sampling is no longer an acceptable testing technique.

There is an increasing need for an evaluation of all critical dimensional criteria of individual threaded fasteners by the suppliers to ensure that defective threaded fasteners are removed before shipment.

As an attempt to provide 100 percent inspection of threaded fasteners, several non-contact inspection systems have been developed for automatically performing various inspections.

U.S. Pat. No. 4,457,622, issued to Kato et al., discloses a screw inspection device, which includes a screw transfer mechanism, a sensor for performing predetermined measurements of the screw during the transfer, a comparator for generating acceptance/non-acceptance signals, and a sorter for classifying the screws into defective and nondefective screws.

U.S. Pat. No. 4,598,998, issued to Kamei et al., discloses an inspection system in which light is projected onto the threaded surface of a fastener, and the surface flaws are detected based on the variation of the intensity of the reflected light.

U.S. Pat. No. 4,823,396, issued to Thompson, discloses an automated inspection device, which includes a camera for producing a video image of a fastener and a computer for comparing the actual dimensions of the fastener with the desired dimensions.

U.S. Pat. No. 5,823,356, issued to Goodrich et al., discloses an inspection device in which threaded fasteners can be continuously supplied and moved into a test station where the threaded profiles of the fasteners are functionally tested. A plurality of sensors are disposed along the transfer path through the inspection device to perform predetermined measurements of the specified dimensional characteristics of the fasteners. A sorting device is disposed close to the end of the transfer path to separate defective fasteners from nondefective ones.

Although conventional non-contact inspection systems are very useful, they all have certain limitations. One limitation is that the types of flaws detected are limited. In order to increase the number of geometry features to be inspected, a complex set-up of sensors and hardware would be required. Another limitation is that the conventional inspection systems are not easily adapted for different fastener sizes and types. In addition, the conventional systems are not capable of inspecting and sorting high volume of small fasteners at high speed.

SUMMARY OF THE INVENTION

The present invention provides a high-speed fastener inspection system that includes a rotary table having an outer periphery, an inner periphery, and a plurality of radial slots extending from the outer periphery to the inner periphery. The radial slots are configured to receive a plurality of fasteners. A loading mechanism, an anti-jam mechanism, and a sorting mechanism are arranged along the outer periphery of the rotary table. A plurality of fasteners are sequentially delivered to the radial slots by the loading mechanism. The anti-jam mechanism is positioned adjacent to the loading mechanism in order to prevent jamming as the fasteners are being delivered to the radial slots. At least one vision inspection camera is provided for capturing the image of each fastener while the fastener is positioned in a radial slot. An image analyzer is operatively connected to the vision inspection camera for analyzing the captured image and to determine whether the fastener is defective. Once the defective fastener has been identified by the image analyzer, the sorting mechanism is actuated to remove the defective fastener from the rotary table. The fastener inspection system of the present invention is adapted to perform 100 percent inspection of various geometry features and to sort a large number of fasteners at high speed.

The advantages and novel features of the present invention will become apparent from the following detailed description of the invention when considered in conjunction with the accompanying drawings.

DETAILED DESCRIPTION OF THE PREFERRED EMBODIMENT

Figure 1:
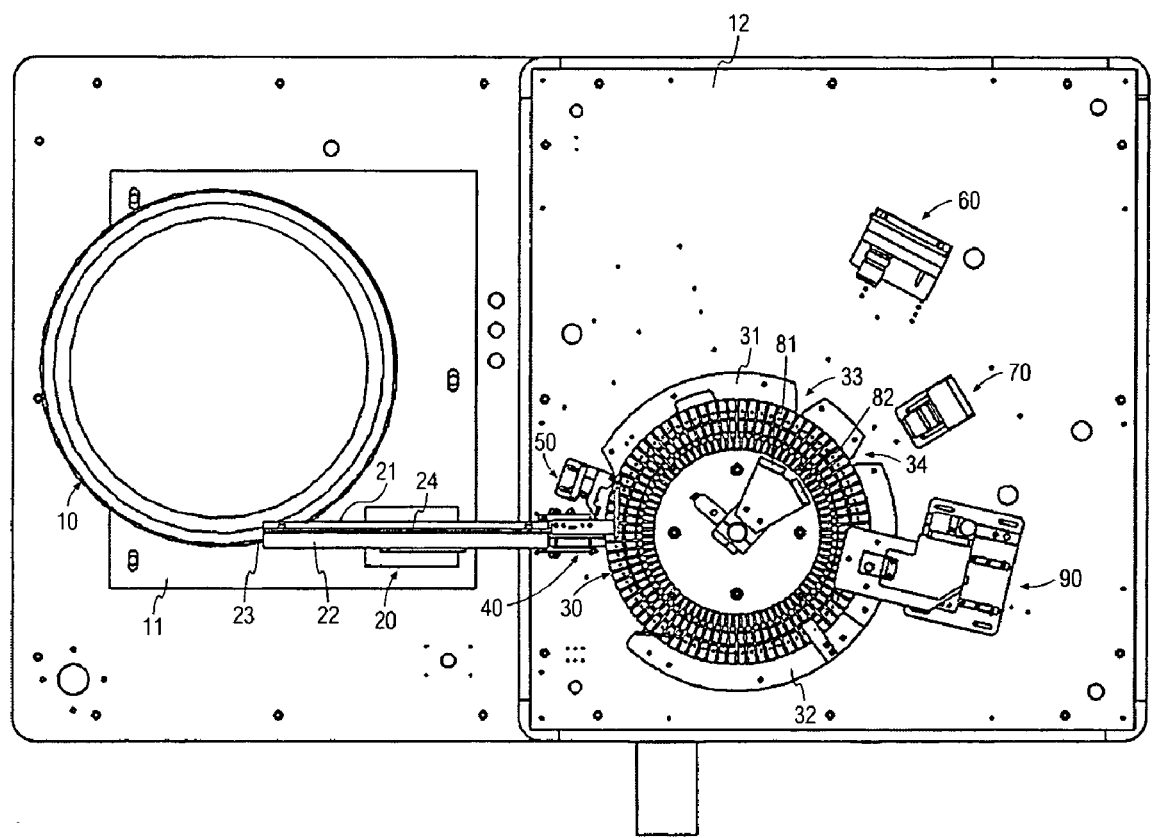
FIG. 1 shows a top plan view of the fastener inspection system according to the preferred embodiment of the present invention.

Referring to FIG. 1, the fastener inspection system according to the preferred embodiment of the present invention is a compact assembly comprising a supply container 10, a transfer mechanism 20, and a wheel-shape rotary table 30 for supporting a plurality of fasteners to be inspected. A loading mechanism 40 is arranged between transfer mechanism 20 and the rotary table 30 in order to load the fasteners, one at a time, from the transfer mechanism 20 onto the rotary table 30. An anti-jam assembly 50 is positioned adjacent to the loading mechanism 40 in order to prevent jamming as the fasteners are being unloaded onto the rotary table 30. Guide frames 31 and 32 are arranged along the periphery of the rotary table 30 for framing a circular path to prevent fastener from falling due to centrifugal force. The inspection equipment includes two side-view inspection cameras 60 and 70, and a top-surface inspection camera 90. A back-light assembly 80 is provided for the side-view inspection cameras 60 and 70. Openings 33 and 34 are provided in the guide frame 31 in order to enable the side-view inspection.

The supply container 10 is preferably a conventional vibratory feeding bowl capable of supplying a large number of fasteners. The transfer mechanism 20 is arranged between the supply container 10 and the rotary table 30 for sequentially conveying the fasteners from the supply container 10 to the rotary table 30. The supply container 10 and the transfer mechanism 20 are mounted on a base 11 while the rotary table 30 is mounted on another base 12. The transfer mechanism 20 has a pair of parallel guide rails 21 and 22, which define a transfer slot 23 there between. The width of the transfer slot 23 is smaller than the diameter of the head of each fastener, but greater than the diameter of the shank so that the heads of the fasteners will be oriented upward and the shanks will be suspended in the slots 23 when the fasteners are moved along the transfer slot 23. The parallel guide rails 21 and 22 are movable relative to each other in order to enable the width of the transfer slot 23 to be varied for different fastener sizes. A top guide rail 24 cooperates with the parallel guide rails 21 and 22 so that the heads of the conveyed fasteners will be held snugly along the transfer slot 23. A closer view of the top guide rail 24 and the parallel guide rails 21 and 22 can be seen in FIG. 4. In order to move the fasteners along the transfer slot 23 downstream toward the rotary table 30, different conventional means may be used. For example, the parallel guide rails 21 and 22 may be inclined from the supply container 10. Alternatively, a vibrator may be attached to the parallel guide rails 21 and 22 in order to vibrate them and move them along the transfer slot 23.

Figure 2:
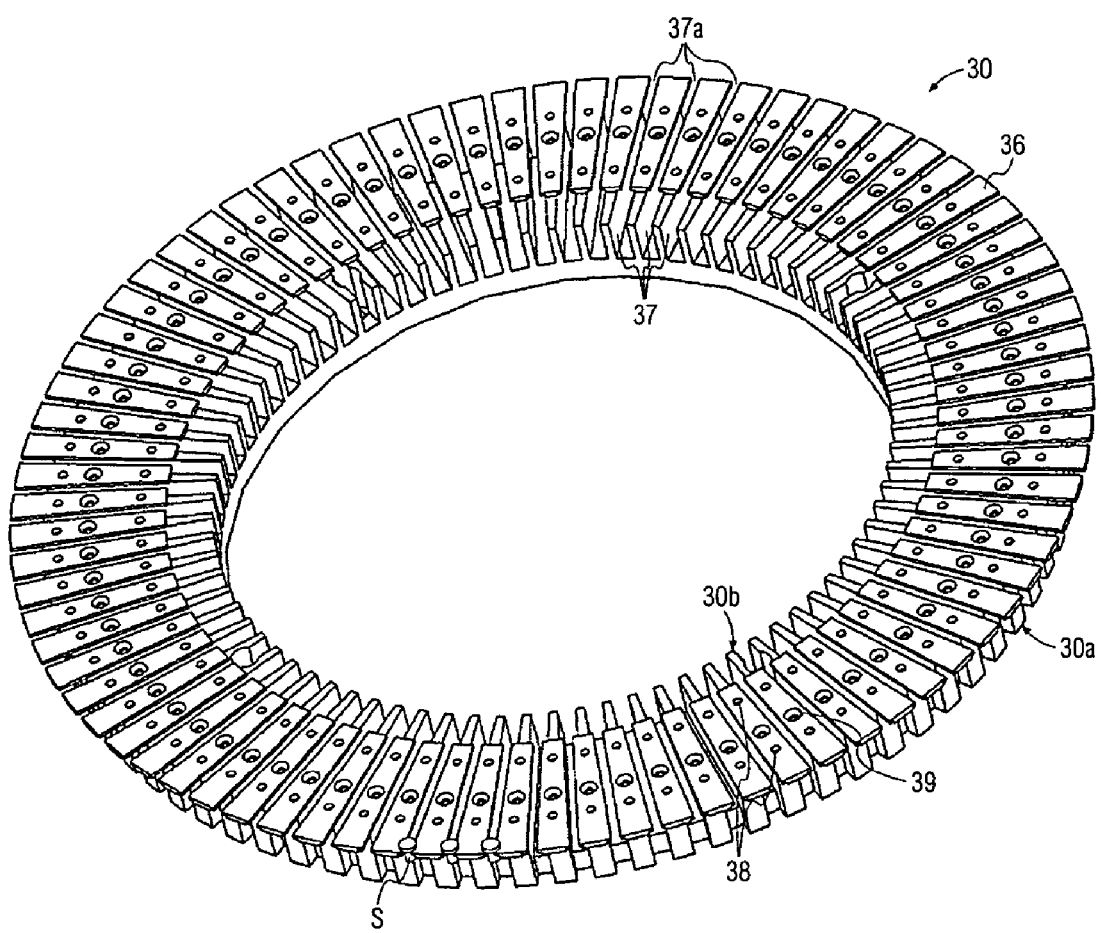
FIG. 2 shows a perspective view of the fastener inspection system according to the preferred embodiment of the present invention.
Figure 3:
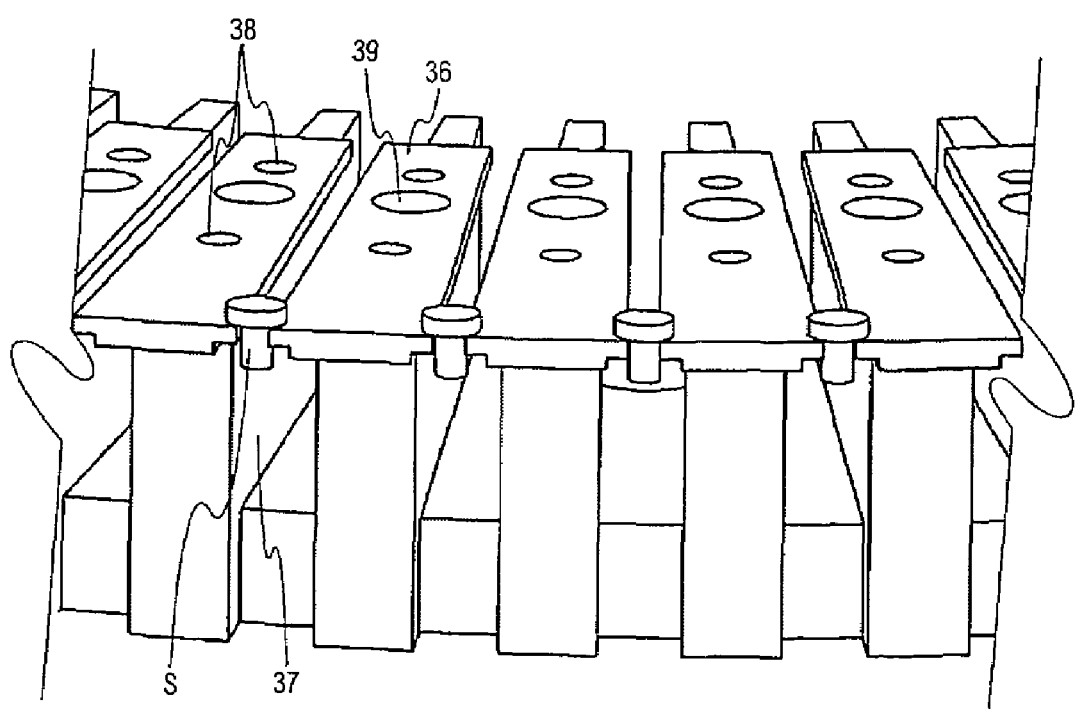
FIG. 3 shows a perspective view of the rotary table according to the preferred embodiment of the present invention.

Referring to FIG. 2, the rotary table 30 has an outer periphery 30a, an inner periphery 30b, and a plurality of radial slots 37 extending from the outer periphery to the inner periphery. A plurality of radial support plates 36 are mounted on top of the rotary table 30 and are spaced from each other so as to define spacings 37a. Each spacing 37a is smaller than the diameter of the head of each fastener but greater than the diameter of the shank. By this arrangement, the heads of the fasteners S could rest on the support plates 36 while the shanks suspend in the slots 37 as shown in FIG. 3. Guide pins 38 are used for positioning the support plates 36 on top of the rotary table 30, and tightening screws 39 are used for securing the support plates 36 to the rotary table 30. The rotary table 30 is rotatable clockwise so that the fasteners S suspended in the radial slots 37 could be conveyed along a circular path in a clockwise direction.

Figure 4:
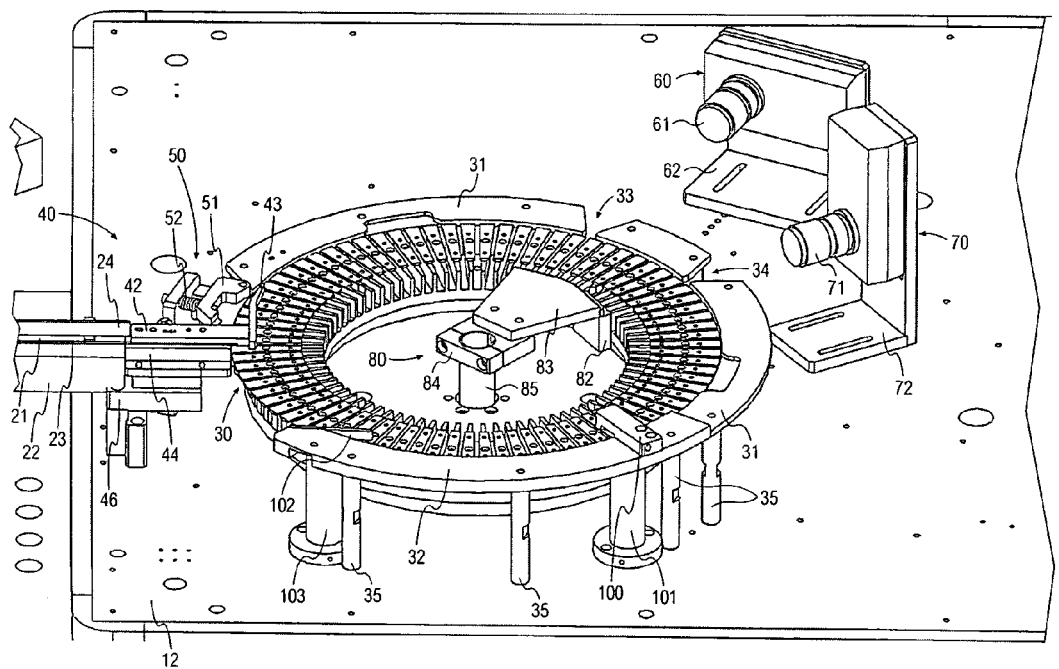
FIG. 4 shows a partial view of the rotary table with the side-view inspection cameras.
Figure 5:
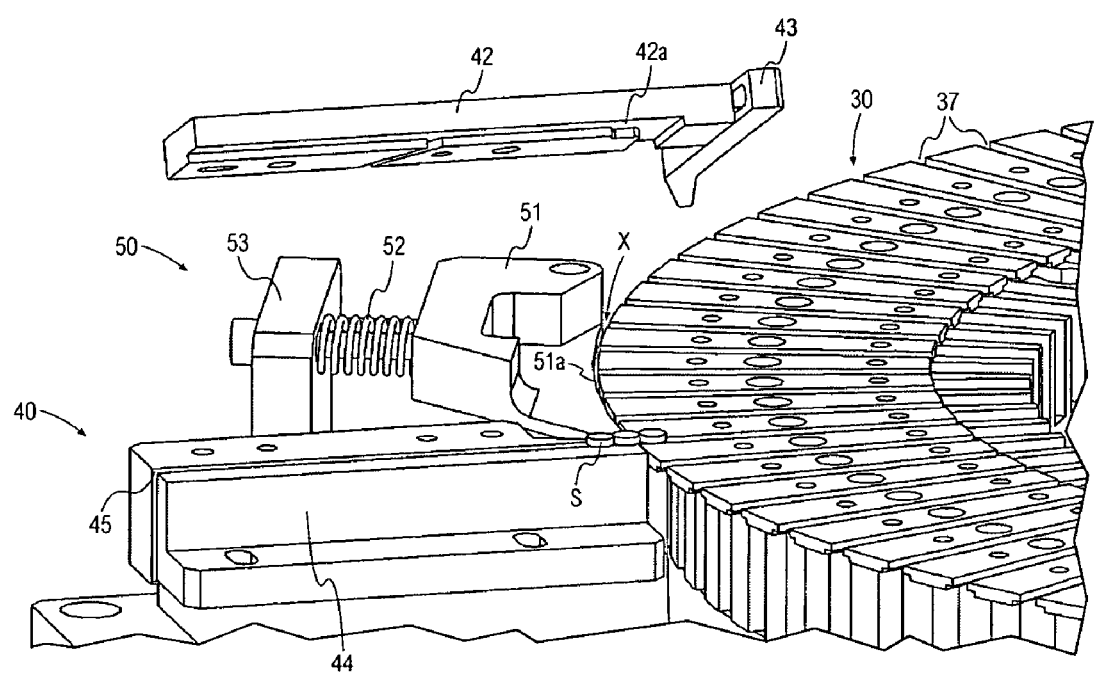
FIG. 5 shows a perspective view of the basic components of the loading mechanism and the anti-jam mechanism according to the preferred embodiment of the present invention.

Referring to FIG. 4, the loading mechanism 40 includes a track top cover 42a and a fixed linear track 44 and The track top cover 42 is attached to a stopper 43. The linear track 44 is mounted onto the base 12 by a mounting assembly 46. The anti-jam mechanism 50 includes a spring-loaded anti-jam arm 51 and a spring 52. FIG. 5 shows the basic components of the loading mechanism 40 with the track top cover 42 detached for illustration. The fixed linear track 44 has a discharge slot 45, which is aligned with the transfer slot 23. The track top cover 42 is provided with a groove 42a for guiding the heads of the fasteners and is replaceable to accommodate different fastener sizes. The track top cover 42 and the linear track 44 cooperate to load the fasteners from the transfer slot 23 sequentially into the radial slots 37. The mechanism used for moving the fasteners along linear track 44 include a vibrator and an air-jet system. During the loading operation, the discharge slot 45 is aligned with a radial slot 37 and one fastener S is moved into the aligned radial slot 37. The rotary table 30 then rotates clockwise so that the adjacent radial slot 37 is aligned with the discharge slot 45 and a subsequent fastener is moved into the adjacent radial slot 37. This loading mechanism is repeated so that the fasteners are continuously and sequentially transferred into the radial slots 37. The stopper 43 is positioned substantially perpendicular to the linear track 44, whereby the newly loaded fasteners are prevented from moving toward the center of the rotary table 30 as the rotary table 30 rotates clockwise. The anti-jam arm 51 is provided with a curved-edge 51a, which substantially follows the curve of the perimeter of the rotary table 30. The anti-jam arm 51 is spring-loaded by the action of a spring 52 so that the anti-jam arm 51 is capable of retracting away from the periphery of the rotary table 30 when the fasteners S are jammed as they exit the discharge slot 45. The fasteners S are jammed when two or more fasteners are moving into the same radial slot 37. When jamming occurs, the anti-jam arm 51 retracts away from the outer periphery of the rotary table 30 so as to allow the jammed fastener to escape into the gap X formed between the curved-edge 51a and the outer periphery of the rotary table 30. The escaped fastener then moves into the adjacent vacant slot 37. The anti-jam arm 51 is mounted to the base 12 by a movable mounting member 53.

Referring again to FIG. 4, the top-surface inspection camera 90 is omitted herein in order to provide an unobstructed view of the side-view inspection cameras 60 and 70. The side-view camera 60 has a lens 61 and is mounted onto the base 12 by bracket 62. The camera 60 is oriented so as to capture an unobstructed side-view image of each fastener when each fastener reaches the location 33. The side-view camera 70 is a close-up view camera, which has a lens 71 and is mounted onto the base 12 by bracket 72. Camera 70 is positioned closer to the rotary table 30 than camera 60 in order to capture a close-up side-view image of each fastener when each fastener reaches opening 34. Back-lights 81 and 82 are positioned within the inner periphery of the rotary table 30, and are oriented so as to shed adequate lighting onto the fasteners at openings 33 and 34 for the cameras 60 and 70. The back-lights 81 and 82 are mounted on bracket 83, which is mounted to the base 12 by assembly members 84 and 85 (back-light 81 can be seen in FIG. 1).

Figure 6:
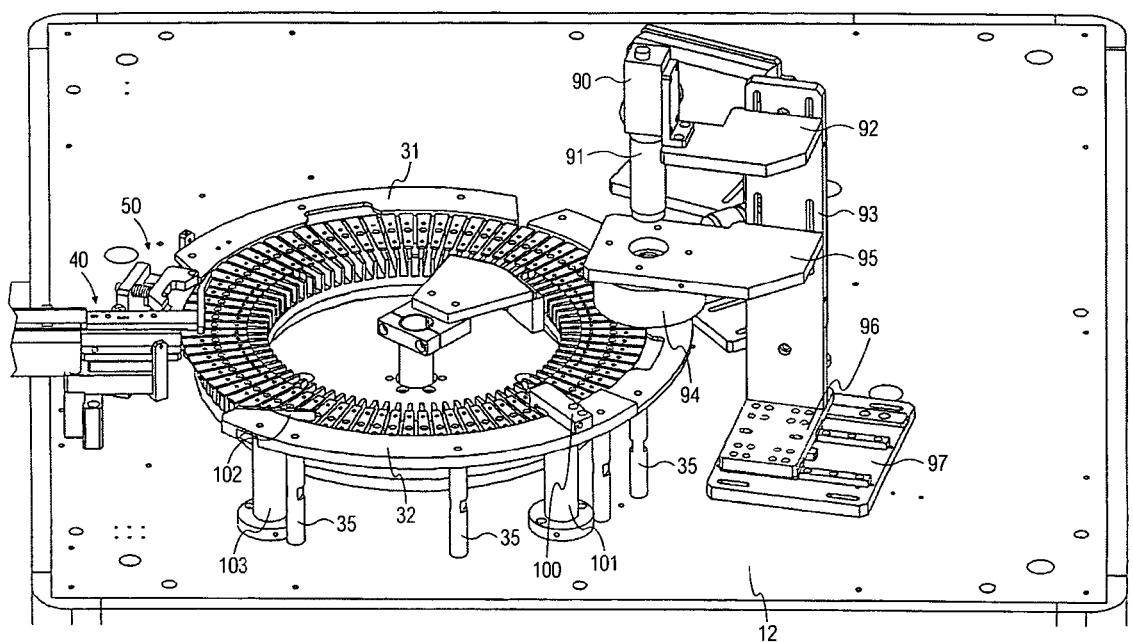
FIG. 6 shows a partial view of the rotary table with the top-surface inspection camera.

Referring to FIG. 6, the top-surface inspection camera 90 has a lens 91 and is held in place by support structures 92 and 93. A customized lighting 93, e.g. ring LED, is provided below the lens 92 in order to provide adequate lighting for the inspection camera 90. The lighting 93 is held in place by bracket 95. The inspection camera 90 is mounted onto a base 96 that is slidable by the action of the mechanical slide 94. The top-surface inspection camera 90 is operable to inspect the top surface of each fastener for crack, recess deformation and contamination.

The guide frames 31 and 32 are supported by a plurality of stand-offs 35. An air-jet supplier 100 is positioned on the guide frame 32 at a spaced distance from the top-surface inspection camera 90. Below the air-jet supplier 100 is a reject chute 101 for receiving the rejected fasteners. The air-jet supplier 90 is operable to direct an air jet onto the rejected fastener so as to blow the rejected fastener into the reject chute 91. A sweeper 102 is attached to the free end of the guide frame 32 and is positioned at a spaced distance from the air-jet supplier 100. An acceptance chute 103 for receiving non-defective fasteners is positioned below the sweeper 102.

The side-view inspection cameras 60 and 70 and the top-surface inspection camera 90 are operatively connected to an image processing computer (not shown) for analyzing the captured images. The computer has the inspection criteria for the acceptable fasteners pre-stored in its memory. The inspection criteria for the side view of the fastener include: head height, head diameter, shank length, thread pitch, underfill, over 1-pitch and other programmable dimensions. From the captured side-view images, the actual dimensions of the fasteners can be obtained. The computer compares the actual dimensions with the pre-stored inspection criteria, then determines whether the fasteners are defective. For the top-surface inspection, crack, contamination, and concentricity can be determined. If a fastener is determined to be defective based on the information received from the side-view inspection or the top surface inspection, then the air-jet supplier 100 is actuated to blow the rejected fastener into the reject chute 101 when such fastener reaches the location below the air-jet supplier 100. If the computer determines that the fastener is acceptable, the acceptable fastener is permitted to remain on the rotary table 30 until the acceptable fastener reaches the sweeper 102, where the acceptable fastener is swept into the acceptance chute 103.

The inspection system of the present invention is capable of fast changeover time for different fastener types and sizes. Other advantages of the inventive system include: quick and easy conversion of pre-programmed inspection criteria; minimum product failure; minimum maintenance; hardware and software can be upgraded.

Although the preferred embodiment of the present invention has been described herein, it should be understood that the invention is not confined to the details and drawings described above, but may be modified within the scope of the appended claims.

The invention claimed is:

1. An inspection system for inspecting and sorting a plurality of fasteners, each fastener having a head and a shank, said system comprising:
   a rotary table having an outer periphery, an inner periphery, and a plurality of radial slots extending from the outer periphery to the inner periphery, each radial slot being configured to receive a fastener with the head of the fastener facing upward and to shank suspending in the radial slot;
   means for rotating the rotary table;
   a loading mechanism for sequentially delivering the fasteners to the radial slots;
   an anti-jam mechanism for preventing jamming as the fasteners are being delivered to the radial slots;
   at least one vision inspection camera operable to capture an image of each fastener after the fastener has been delivered to a radial slot;
   an image analyzer operatively connected to said at least one vision inspection camera for analyzing the captured image and to determine whether the fastener shown in the captured image is defective; and
   a sorting mechanism for removing any defective fastener from the rotary table when the defective fastener has been identified by the image analyzer,
   wherein the loading mechanism, the anti-jam mechanism and the sorting mechanism are positioned along the outer periphery of the rotary table,
   wherein the anti-jam mechanism comprises an anti-jam arm having a curved edge positioned adjacent to the outer periphery of the rotary table, and the anti-jam arm being spring-loaded so that the curved edge can retract away from the outer periphery of the rotary table when the fasteners are jammed.

2. The inspection system of claim 1 further comprising:
   a sweeper positioned along the outer periphery of the rotary table at a location between the loading mechanism and the sorting mechanism; and
   an acceptance chute positioned adjacent to the sweeper, wherein the sweeper is adapted for sweeping the non-defective fasteners from the rotary table into the acceptance chute.

3. The inspection system of claim 1, wherein two side-view inspection cameras are provided, one of the cameras being closer to the outer periphery of the rotary table than the other, and the image analyzer is operatively connected to both side-view inspection cameras.

4. The inspection system of claim 1, wherein said side-view inspection cameras capture unobstructed image of each said fastener after the fastener has been delivered to a radial slot.

5. The inspection system of claim 1, wherein a top-surface inspection camera is provided for inspecting the top surface of each fastener.

6. The inspection system of claim 1, wherein the unloading mechanism comprises:
   a linear track with a discharge slot for guiding the fasteners toward the rotary table, said linear track having a downstream end that is positioned adjacent to the outer periphery of the rotary table, and said discharge slot having a width that is smaller than the head diameter of each fastener but greater than the diameter of the shank;
   a track top cover mounted on the linear track for covering the discharge slot; and
   a stopper positioned adjacent to the downstream end of the linear track so as to prevent each fastener from moving toward the inner periphery of the rotary table after each fastener has been transferred into a radial slot.

7. The inspection system of claim 6, wherein the anti-jam arm is positioned adjacent to the linear track.

8. The inspection system of claim 1, wherein the sorting mechanism comprises:
   an air-jet supplier for blowing the defective fastener from the rotary table; and
   a reject chute positioned adjacent to the air-jet supplier for receiving the defective fastener.

9. The inspection system of claim 1, wherein the rotary table is provided with a plurality of support plates radially arranged on the rotary table so that a spacing is defined between adjacent support plates, each spacing having a width that is smaller than the diameter of the head of each fastener but greater than the diameter of the shank, and each spacing being aligned with each radial slot in a manner that enable the heads of the fasteners to rest on the support plates while the shanks extend into the radial slots.

10. The inspection system of claim 1 further comprising:
   a vibratory supply bowl for supplying a plurality of fasteners; and
   a pair of parallel guide rails defining a transfer slot there between,
   wherein the parallel guide rails are arranged between the vibratory, supply bowl and the loading mechanism so that the fasteners may be sequentially fed from the vibratory supply bowl along the transfer slot to the loading mechanism.

11. The inspection system of claim 1 further comprising a light for illuminating each fastener as said at least one vision inspection camera is capturing the side view image of the fastener.

12. A method for automatically inspecting and sorting a plurality of fasteners, said method comprising:
  providing a rotary table having an outer periphery, an inner periphery, and a plurality of radial slots extending from the outer periphery to the inner periphery, each radial slot being configured to receive a fastener;
  providing an anti-jam mechanism positioned along the outer periphery, the anti-jam mechanism comprises an anti-jam arm;
  rotating the rotary table;
  sequentially delivering a plurality of fasteners into the radial slots, one fastener per slot;
  operating at least one vision inspection camera to capture an unobstructed side-view image of each fastener after each fastener has been delivered to a radial slot;
  analyzing the captured image to determine whether the fastener shown in the captured image is defective;
  removing any defective fastener from the rotary table when the defective fastener has been identified; and
  collecting the non-defective fasteners on the rotary table,
  wherein the anti-jam arm is having a curved edge positioned adjacent to the outer periphery of the rotary table and the anti-jam arm is spring-loaded so that the curved edge can retract away from the outer periphery of the rotary table when the fasteners are jammed.

13. A method for automatically inspecting and sorting a plurality of fasteners, said method comprising:
  providing a rotary table having an outer periphery, an inner periphery, and a plurality of radial slots extending from the outer periphery to the inner periphery, each radial slot being configured to receive a fastener;
  rotating the rotary table;
  providing a loading mechanism for sequentially delivering the fasteners to the radial slots;
  providing an anti-jam mechanism for preventing jamming as the fasteners are being delivered to the radial slots;
  wherein the anti-jam mechanism comprises an anti-jam arm having a curved edge positioned adjacent to the outer periphery of the rotary table, and the anti-jam arm being spring-loaded so that the curved edge can retract away from the outer periphery of the rotary table when the fasteners are jammed;
  providing at least one vision inspection camera operable to capture a slide view image of each fastener after the fastener has been delivered to a radial slot;
  providing an image analyzer operatively connected to said at least one vision inspection camera for analyzing the captured image;
  analyzing the captured image to determine whether the fastener shown in the captured image is defective; and
  providing a sorting mechanism for removing any defective fastener from the rotary table when the defective fastener has been identified by the image analyzer; and inspecting a plurality of fasteners using said inspection system; and separating any defective fastener from the inspected fasteners.

* * * * *

UNITED STATES PATENT AND TRADEMARK OFFICE
CERTIFICATE OF CORRECTION

| | | |
|---|---|---|
| PATENT NO. | : 7,364,043 B2 | Page 1 of 1 |
| APPLICATION NO. | : 10/747441 | |
| DATED | : April 29, 2008 | |
| INVENTOR(S) | : Hock Seh Ong and Ta Seng Jeffrey Mah | |

It is certified that error appears in the above-identified patent and that said Letters Patent is hereby corrected as shown below:

Column 7, line 28, delete "is having" and replace with --has--

Column 8, line 19, delete "slide" and replace with --side--

Signed and Sealed this

Twenty-sixth Day of August, 2008

JON W. DUDAS
*Director of the United States Patent and Trademark Office*